United States Patent
Jahns et al.

(10) Patent No.: US 12,390,312 B2
(45) Date of Patent: Aug. 19, 2025

(54) SET OF COLORED POROUS ZIRCONIA DENTAL MILL BLANKS AND PROCESS OF PRODUCTION

(71) Applicant: Solventum Intellectual Properties Company, Maplewood, MN (US)

(72) Inventors: Michael Jahns, Gilching (DE); Hans R. Schnagl, Jengen (DE); Gallus Schechner, Herrsching (DE)

(73) Assignee: Solventum Intellectual Properties Company, Maplewood, MN (US)

( * ) Notice: Subject to any disclaimer, the term of this patent is extended or adjusted under 35 U.S.C. 154(b) by 0 days.

(21) Appl. No.: 18/029,975

(22) PCT Filed: Sep. 23, 2021

(86) PCT No.: PCT/IB2021/058689
§ 371 (c)(1),
(2) Date: Apr. 3, 2023

(87) PCT Pub. No.: WO2022/074494
PCT Pub. Date: Apr. 14, 2022

(65) Prior Publication Data
US 2023/0338123 A1   Oct. 26, 2023

(30) Foreign Application Priority Data
Oct. 9, 2020   (EP) .................................. 20200937

(51) Int. Cl.
*A61C 13/00* (2006.01)
*A61K 6/15* (2020.01)
(Continued)

(52) U.S. Cl.
CPC .......... *A61C 13/0022* (2013.01); *A61K 6/15* (2020.01); *A61K 6/818* (2020.01); *A61K 6/82* (2020.01); *A61K 6/822* (2020.01)

(58) Field of Classification Search
CPC .................. A61C 13/00; A61K 6/818; C04B 2235/3244; C04B 2237/348; C04B 2237/582; C04B 2237/58
See application file for complete search history.

(56) References Cited

U.S. PATENT DOCUMENTS

| 7,985,119 B2 | 7/2011 | Basler et al. |
| 8,141,217 B2 | 3/2012 | Gubler et al. |
(Continued)

FOREIGN PATENT DOCUMENTS

| DE | 20316004 U1 | 3/2004 |
| EP | 2024300 B1 | 3/2013 |
(Continued)

OTHER PUBLICATIONS

1507 Extended EP Search Report for EP20200937.9, Date Apr. 1, 2021, 3pgs.
(Continued)

*Primary Examiner* — Maria V Ewald
*Assistant Examiner* — Daniel P Dillon

(57) ABSTRACT

The invention relates to a set of porous zirconia dental mill blanks comprising at least two differently colored porous zirconia dental mill blanks, the porous zirconia dental mill blanks comprising zirconia, yttria, coloring ions, and optionally alumina, comprising multiple layers with different yttria content, having a bottom layer and a top layer, the content of yttria and coloring ions in mol % changing in opposite direction to each other from the bottom layer to the top layer, and the content of yttria and coloring ions in mol % being adjusted to provide an essentially constant ratio of the sum of yttria and coloring ions in mol % between the top layer and the bottom layer for the at least two differently colored zirconia dental mill blanks. The invention also relates to a process of producing such a set.

14 Claims, 1 Drawing Sheet

(51) Int. Cl.
    *A61K 6/818*     (2020.01)
    *A61K 6/82*     (2020.01)
    *A61K 6/822*     (2020.01)

(56) References Cited

U.S. PATENT DOCUMENTS

| | | | |
|---|---|---|---|
| 9,212,065 B2 * | 12/2015 | Yamada | C04B 35/486 |
| 9,649,179 B2 * | 5/2017 | Jung | C04B 35/486 |
| 10,238,473 B2 | 3/2019 | Jung et al. | |
| 10,426,583 B2 | 10/2019 | Jung et al. | |
| 2009/0130634 A1 * | 5/2009 | Ganley | A61C 13/0022 |
| | | | 433/206 |
| 2014/0300014 A1 | 10/2014 | Tanaka | |
| 2016/0120765 A1 | 5/2016 | Dang et al. | |
| 2016/0157971 A1 | 6/2016 | Rothbrust et al. | |
| 2018/0002235 A1 * | 1/2018 | Ito | A61C 8/0012 |
| 2018/0125616 A1 | 5/2018 | Kitamura et al. | |
| 2018/0263863 A1 | 9/2018 | Kim et al. | |
| 2019/0321146 A1 | 10/2019 | Jung et al. | |
| 2019/0380815 A1 * | 12/2019 | Aiba | C04B 35/62645 |
| 2021/0290351 A1 * | 9/2021 | Voelkl | C04B 35/46 |

FOREIGN PATENT DOCUMENTS

| | | |
|---|---|---|
| EP | 3108849 A1 | 12/2016 |
| EP | 3246300 A1 | 11/2017 |
| EP | 2829251 B1 | 4/2019 |
| EP | 3567017 A1 | 11/2019 |
| EP | 2995434 B1 | 2/2020 |
| EP | 3006418 B1 | 1/2022 |
| JP | 2017113224 A | 6/2017 |
| JP | 2018080160 A | 5/2018 |
| WO | 2001013862 A1 | 3/2001 |
| WO | 2002045614 A1 | 6/2002 |
| WO | 2017144644 A1 | 8/2017 |
| WO | 2019180766 A1 | 9/2019 |

OTHER PUBLICATIONS

International Search Report for PCT International Application No. PCT/IB2021/058689, mailed on Dec. 14, 2021, 4 pages.

* cited by examiner

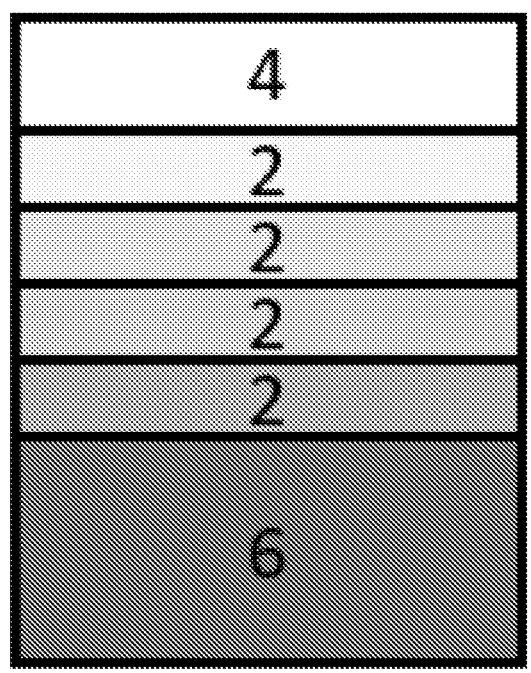

SET OF COLORED POROUS ZIRCONIA DENTAL MILL BLANKS AND PROCESS OF PRODUCTION

CROSS REFERENCE TO RELATED APPLICATIONS

This application is a national stage filing under 35 U.S.C. 371 of PCT/US2021/058689, filed Sep. 23, 2021, which claims the benefit of European Application No. 20200937.9, filed Oct. 9, 2020, the disclosures of which are incorporated by reference in their entireties herein.

FIELD OF THE INVENTION

The invention relates to a set of porous zirconia dental mill blanks comprising at least two differently colored porous zirconia dental mill blanks, a process for producing such a set, a process of producing a dental restoration from such a set and a kit of parts comprising such a set and a dental cement.

BACKGROUND

There is a continued demand for an improved esthetic appearance of dental zirconia restorations, in particular monolithic dental zirconia restorations.

To bring zirconia materials a step closer to the appearance of natural teeth, zirconia with different translucency levels in one restoration can be used to mimic the natural transition from dentin to enamel.

In this respect various processes and materials are suggested.

US 2016/0120765 A1 (Dang et al.) describes a dental article for producing a dental prosthesis, the dental article comprising: a first layer comprising yttria in an amount of a first weight percentage and zirconia oxide particles; a second layer comprising yttria in an amount of a second weight percentage and the zirconia oxide particles; and a third layer comprising yttria in an amount of a third weight percentage and the zirconia oxide particles, wherein: the first layer is located below the second layer and the third layer, the second layer is located between the first layer and the third layer, and at least one of the first layer, the second layer, and the third layer comprises a pigment in an amount of a certain weight percentage.

WO 2019/180766 A1 (Tosoh) relates to a zirconia sintered body having both translucency and high strength and a method for producing the same, which can be produced by controlling the state of the raw material powder, e.g. by using a first zirconia powder having a yttria content of 2 to 4 mol % inclusive and a second zirconia powder having a yttria content of more than 4 mol % and equal to or lower than 6 mol %, and has a yttria content of more than 3 mol % and equal to or less than 5.2 mol %.

US 2019/0380815 A1 (Aiba et al.) describes a dental zirconia blank having a plurality of layers, comprising: a first layer consisting of a high permeability ceramic containing 91.6 to 96.5 mol % of zirconium oxide and 3.5 to 8.4 mol % of yttrium oxide, and a second layer consisting of a low permeability ceramic containing 95.6 to 98.5 mol % of zirconium oxide and 1.5 to 4.4 mol % of yttrium oxide, wherein a content rate of yttrium oxide in the low permeability ceramic is lower than a content rate of yttrium oxide in the high permeability ceramic by 0.5 to 5.4 mol %, and the first layer is positioned at one end of the plurality of layers in a layering direction.

US 2018/0263863 A1 (Kim et al.) describes a method for enhancing optical properties of sintered, zirconia ceramic bodies and zirconia ceramic dental restorations is provided. Method steps comprise a) applying a first yttrium-containing composition onto a surface of a pre-sintered or porous ceramic body; b) applying a second yttrium-containing composition onto the pre-sintered or porous ceramic body; and c) sintering the ceramic body.

US 2019/0321146 A1 (Jung et al.) relates to a green body zirconia dental blank with chemical compositions of increasing amounts of yttria through a thickness thereof and a pre-sintered optical characteristic of chroma that is substantially consistent and white across the thickness; and being milled, colored and sintered to form the dental prosthesis with an optical characteristic of decreasing chroma through a thickness of the dental prosthesis after sintering.

US 2016/157971 A1 (Rothbrust et al.) describes a process comprising (a) providing at least a first oxide ceramic material and a second oxide ceramic material, wherein the first oxide ceramic material and the second oxide ceramic material differ in terms of a sintering behavior; and (b) adapting at least one of the oxide ceramic materials to align the sintering behavior of the first oxide ceramic material to the sintering behavior of the second oxide ceramic material.

US 2018/002235 A1 (Ito et al.) describes a partially stabilized zirconia sintered body, comprising 4 mol % to 7 mol % of yttria as a stabilizer, wherein the zirconia sintered body comprises a light shielding material, the zirconia sintered body has a first region, and a second region having a higher content ratio of the light shielding material than the first region, and a difference between a content ratio of yttria in the first region and a content ratio of yttria in the second region is 1 mol % or less.

U.S. Pat. No. 10,238,473 (Jung et al.) describes a zirconia sintered body, comprising: a) a sintered body comprising zirconia; b) the sintered body having multiple different areas, including at least one upper area and at least one lower area; c) the at least one upper area and the at least one lower area have a different chemical composition therebetween, with at least one area having a different strength that another area; and d) the sintered body having a translucency and a strength with an inverse relationship, with the translucency increasing in one direction across the multiple different areas and the strength decreasing in the same direction across the multiple different areas.

EP 3 108 849 A1 (3M) describes a porous multi-layered coloured zirconia dental mill blank comprising a bottom layer B, a top layer E, at least one intermediate layer $E_x$ and at least one intermediate layer $B_x$ wherein the layers are arranged in alternating order and wherein the thickness of the individual layers B, $B_x$ is decreasing from bottom to up and the thickness of the individual layers E, $E_x$ is decreasing from top to bottom.

SUMMARY OF INVENTION

It can be challenging to provide an esthetically pleasing dental restoration by layering different zirconia compositions with different yttria content.

Several factors have to be considered, e.g. the difference in yttria content between the layers and the interaction of yttria content and coloring components for each layer.

Sometimes the interface between differently doped material layers looks opaque or produces other undesired optical effects in the material. It is speculated that the observed effect arises from a too high difference in yttria doping between the layers.

Higher doping with coloring components will reduce the relative amount of yttria. Furthermore, the sum of yttria and coloring components may be higher than the amount of yttria alone, but with the darker color caused by the coloring components, the resulting translucency is usually lower and not higher in spite of the higher amounts of dopants.

Manufacturers of dental mill blanks are thus confronted with the object of providing dental mill blanks which after machining and sintering result in dental restorations having the desired translucency for different tooth shades.

It would be desirable if the translucency gradient could be improved, i.e. be clearly visible, and at the same time be as similar as possible for a large variety of dental colors, e.g. from very light to very dark colors.

The same is valid for the strength of the material. Different amounts of additives (e.g. coloring ions and stabilizer) usually lead to a different strength of the ceramic. It is desirable, that this difference is predictable for a large variety of dental colors, e.g. from very light to very dark colors.

However, the different amounts of additives (e.g. coloring ions and stabilizer) being present within a dental mill blank can have an impact on the sintering behaviour. Depending on the chemical compositions in a blank, sometimes distortions in the ceramic can occur during sintering.

Thus, there is a need for a set of dental mill blanks, which yield aesthetically pleasing results, are reliable regarding translucency and strength, can be produced easily and can be sintered reliably.

The invention described in the present text addresses this object by providing a set of colored zirconia dental mill blanks comprising yttria and coloring ions in a certain ratio. This ratio is preferably as high as possible and as constant as possible for the set of mill blanks having a large variety of dental colors, e.g. from very light to very dark colors.

In one embodiment the present invention features a set of porous zirconia dental mill blanks comprising at least two differently colored porous zirconia dental mill blanks,
the porous zirconia dental mill blanks
comprising zirconia, yttria, coloring ions, and optionally alumina,
comprising multiple layers with different yttria content, having a bottom layer and a top layer,
the content of yttria and coloring ions in mol % changing in opposite direction to each other from the bottom layer to the top layer, and
the content of yttria and coloring ions in mol % being adjusted to provide an essentially constant ratio of the sum of yttria and coloring ions in mol % between the top layer and the bottom layer for the differently colored zirconia dental mill blanks.

The invention also relates to a process of producing a set of porous zirconia dental mill blanks as described in the present text, the process comprising the steps of
providing at least the following powder compositions:
zirconia powder ZP1 having an yttria content Y1,
zirconia powder ZP2 having an yttria content Y2,
zirconia powder ZP3 containing coloring ions CI-A,
zirconia powder ZP4 containing coloring ions CI-B,
the yttria content Y2 in mol % being higher than the yttria content Y1,
mixing the zirconia powders ZP1, ZP2, ZP3, and ZP4 with different mixing ratios to obtain at least
a zirconia powder composition ZP-MX-B,
a zirconia powder composition ZP-MX-Im,
a zirconia powder composition ZP-MX-T,
the yttria content in mol % of the zirconia powder compositions being $$ZP\text{-}MX\text{-}B < ZP\text{-}MX\text{-}I_m < ZP\text{-}MX\text{-}T,$$

the number of intermediate layers being M≥1 with m=1, M,
for each colored porous zirconia dental mill blank of the set layering the zirconia powder compositions in the cavity of a mould so that
the layer of ZP-MX-B is located below the layer(s) of ZP-MX-$I_m$,
the layer(s) of ZP-MX-$I_m$ is located below the layer of ZP-MX-T
compacting the layered zirconia powder compositions,
optionally heat-treating the compacted zirconia powder compositions.

A further embodiment of the invention is directed to a process of producing a dental restoration, the process comprising the steps of
providing the set of porous zirconia dental mill blanks as described in the present text,
selecting or choosing from the set a porous zirconia dental mill blank,
machining a porous dental restoration precursor from the porous zirconia dental mill blank,
sintering the porous dental restoration precursor to obtain a dental restoration.

Further, the invention relates to a kit of parts comprising the set of porous zirconia dental mill blanks as described in the present text and a dental cement.

Unless defined differently, for this description the following terms shall have the given meaning:

The term "dental article" means an article which is to be used in the dental or orthodontic field, especially for producing of or as dental restoration, a tooth model and parts thereof.

A "dental restoration" means a dental article for restoring a defective tooth structure. A dental restoration typically has a 3-dimensional inner and outer surface. The surface typically includes convex and concave structures. Compared to other articles such as pottery or paving stones, a dental restoration is small and filigree. The thickness of the dental restoration can vary from very thin, e.g. at the edges and rims (below 0.1 mm) to considerably thick, e.g. in the biting area (up to 8 or 16 mm). Sections bridging the crown portions in dental bridges might have a thickness up to 20 mm. The outer surface typically has an overall convex shape, whereas the inner surface typically has an overall concave shape.

The dental restoration described in the present text comprises or essentially consists after sintering of a polycrystalline ceramic material comprising yttrium stabilized zirconia.

Examples of dental articles include crowns (including monolithic crowns), bridges, inlays, onlays, veneers, facings, copings, crown and bridge framework, implants, abutments, orthodontic appliances (e.g. brackets, buccal tubes, cleats and buttons), monolithic dental restorations (i.e. restorations which do not need to be veneered) and parts thereof.

The surface of a tooth is considered not to be a dental article.

A dental article should not contain components which are detrimental to the patient's health and thus free of hazardous and toxic components being able to migrate out of the dental article.

By "dental mill blank" is meant a solid block (3-dim article) of material from which a dental article, dental workpiece, dental support structure or dental restoration can and typically is to be machined in any subtractive process, e.g. besides milling also by grinding, drilling etc.

A dental mill blank has a geometrically defined shape and comprises at least one flat surface. A so-called "free form surface" is not regarded as "geometrically defined". In this respect the shape of a dental restoration (e.g. crown or bridge) itself is not regarded a dental mill blank.

"Zirconia article" shall mean a 3-dimensional article wherein at least one the x,y,z dimensions is at least about 5 mm, the article being comprised of at least 80 or at least 90 or at least 95 wt. % zirconia.

"Ceramic" means an inorganic non-metallic material that is produced by application of heat. Ceramics are usually hard, porous and brittle and, in contrast to glasses or glass ceramics, display an essentially purely crystalline structure.

"Crystalline" means a solid composed of atoms arranged in a pattern periodic in three dimensions (i.e., has long range crystal structure as determined by X-ray diffraction). Crystal structures include tetragonal, monoclinic, cubic zirconia and mixtures thereof.

"Monolithic dental restoration" shall mean a dental ceramic article onto the surface of which no facing or veneer has been attached. That is, the monolithic dental restoration is essentially comprised out of only one material composition. However, if desired a thin glazing layer can be applied.

"Glass" means an inorganic non-metallic amorphous material which is thermodynamically an under-cooled and frozen melt. Glass refers to a hard, brittle, transparent solid. Typical examples include soda-lime glass and borosilicate glass. A glass is an inorganic product of fusion which has been cooled to a rigid condition without crystallizing. Most glasses contain silica as their main component and a certain amount of glass former and modifier.

The porous ceramic dental material described in the present text does not contain a glass.

"Glass-ceramic" means an inorganic non-metallic material where one or more crystalline phases are surrounded by a glassy phase so that the material comprises a glass material and a ceramic material in a combination or mixture. It is formed as a glass, and then made to crystallize partly by heat treatment. Glass ceramics may refer to a mixture of lithium-, silicon-, and aluminium-oxides.

The porous dental material described in the present text does not contain a glass-ceramic.

A "powder" means a dry, bulk composed of a large number of fine particles that may flow freely when shaken or tilted.

A "particle" means a substance being a solid having a shape which can be geometrically determined. The shape can be regular or irregular. Particles can typically be analysed with respect to e.g. size and size distribution.

"Density" means the ratio of mass to volume of an object. The unit of density is typically $g/cm^3$. The density of an object can be calculated e.g. by determining its volume (e.g. by calculation or applying the Archimedes principle or method) and measuring its mass.

The volume of a sample can be determined based on the overall outer dimensions of the sample. The density of the sample can be calculated from the measured sample volume and the sample mass. The total volume of the ceramic material can be calculated from the mass of the sample and the density of the used material. The total volume of cells in the sample is assumed to be the remainder of the sample volume (100% minus the total volume of material).

A "porous material" refers to a material comprising a partial volume that is formed by voids, pores, or cells in the technical field of ceramics. Accordingly, an "open-celled" structure of a material sometimes is referred to as "open-porous" structure, and a "closed-celled" material structure sometimes is referred to as a "closed-porous" structure. It may also be found that instead of the term "cell" sometimes "pore" is used in this technical field. The material structure categories "open-celled" and "closed-celled" can be determined for different porosities measured at different material samples (e.g. using a mercury "Poremaster 60-GT" from Quantachrome Inc., USA) according to DIN 66133. A material having an open-celled or open-porous structure can be passed through by e.g. gases.

Typical values for an "open-celled" material are between 15% and 75% or between 18% and 75%, or between 30% and 70%, or between 34% and 67%, or between 40% to 68%, or between 42% and 67%. The term "closed-celled" relates to a "closed porosity". Closed cells are those cells which are not accessible from the outside and cannot be infiltrated by gases under ambient conditions.

The "average connected pore diameter" means the average size of the open-celled pores of a material. The average connected pore diameter can be calculated as described in the Examples section.

"Calcining" refers to a process of heating a solid material to drive off at least 90 percent by weight of volatile chemically bond components (e.g. organic components) (vs., for example, drying, in which physically bonded water is driven off by heating). Calcining is done at a temperature below a temperature needed to conduct a pre-sintering step.

The terms "sintering" or "firing" are used interchangeably. A pre-sintered ceramic article shrinks during a sintering step, that is, if an adequate temperature is applied. The sintering temperature to be applied depends on the ceramic material chosen. For zirconia based ceramics a typical sintering temperature range is from 1,100° C. to 1,600° C. Sintering typically includes the densification of a porous material to a less porous material (or a material having less cells) having a higher density, in some cases sintering may also include changes of the material phase composition (for example, a partial conversion of an amorphous phase toward a crystalline phase).

A "fluorescing agent" shall mean an agent showing or providing fluorescence in the region of visible light (380 to 780 nm).

By "machining" is meant milling, grinding, cutting, carving, or shaping a material by a machine. Milling is usually faster and more cost effective than grinding. A "machinable article" is an article having a 3-dimensional shape and having sufficient strength to be machined.

"Ambient conditions" mean the conditions which the inventive solution is usually subjected to during storage and handling. Ambient conditions may, for example, be a pressure of 900 to 1,100 mbar, a temperature of 10 to 40° C. and a relative humidity of 10 to 100%. In the laboratory ambient conditions are adjusted to 20 to 25° C. and 1,000 to 1,025 mbar at maritime level.

A composition is "essentially or substantially free o" f a certain component, if the composition does not contain said component as an essential feature. Thus, said component is not wilfully added to the composition either as such or in combination with other components or ingredient of other components. A composition being essentially free of a certain component usually does not contain that component at all. However, sometimes the presence of a small amount of the said component is not avoidable e.g. due to impurities contained in the raw materials used.

As used herein, "a", "an", "the", "at least one" and "one or more" are used interchangeably.

The terms "comprise" or "contain" and variations thereof do not have a limiting meaning where these terms appear in the description and claims. "Consisting essentially of" means that specific further components can be present, namely those which do not materially affect the essential characteristic of the article or composition. "Consisting of" means that no further components should be present. The term "comprise" shall include also the terms "consist essentially of" and "consists of".

The recitations of numerical ranges by endpoints include all numbers subsumed within that range (e.g., 1 to 5 includes 1, 1.5, 2, 2.75, 3, 3.80, 4, 5, etc.).

Adding an "(s)" to a term means that the term should include the singular and plural form. E.g. the term "additive(s)" means one additive and more additives (e.g. 2, 3, 4, etc.).

Unless otherwise indicated, all numbers expressing quantities of ingredients, measurement of physical properties such as described below and so forth used in the specification and claims are to be understood as being modified in all instances by the term "about".

BRIEF DESCRIPTION OF FIGURES

FIG. 1 schematically shows a multi-layered dental mill blank with a color and translucency gradient.

DETAILED DESCRIPTION

The invention described in the present text is advantageous for a couple or reasons: As the porous dental mill blank comprises multiple layers with different yttria content, the dental mill blank or a dental article machined thereof will show a translucency gradient after sintering. In addition, as the amounts of yttria and coloring ions change in opposite direction to each other from the bottom layer to the top layer, the dental mill blank or a dental article machined thereof will show a color gradient after sintering.

The translucency and/or color gradient obtained after sintering is pretty similar to the translucency and color gradient of a natural tooth.

Furthermore, as the ratio of the sum of yttria and coloring ions between the top layer and bottom layer is essentially constant for the dental mill blanks of the set, the differently colored zirconia mill blanks can be sintered at essentially the same conditions reducing the risk of discoloration and/or distortions.

It was found that by using certain molar ratios of yttria and coloring components, a higher stability of the overall dopant amounts across different shades (from very light to very dark) can be achieved. With this, the intensity and the reliability of the translucency gradient can be improved for a large variety of dental colors (from very light to very dark).

The invention is directed to a set of porous zirconia dental mill blanks.

The set comprises at least two differently colored zirconia dental mill blanks. The set may comprise at least 3, 4, 5, 6, 7, 8, 9, 10, 15, 16 or 17 differently colored zirconia dental mill blanks.

Differently colored means that the individual zirconia dental mill blanks can be distinguished from each other by the color which is obtained after having conducted a sintering process.

The porous zirconia dental mill blanks have a bottom layer and a top layer. The bottom and the top layer correspond to individual layers. If there are more than two layers, the further layers are referred to as intermediate layers.

The porous zirconia dental mill blanks comprise multiple layers with different yttria content.

The porous zirconia dental mill blanks typically comprises at least 3 or 4 or 5 layers. Usually, a porous zirconia dental mill blank comprises 3 to 8 or 4 to 7 layers.

The thickness of the individual layers of the porous zirconia dental mill blank is typically in a range of 2 to 12 mm or 2 to 10 mm, or 2 to 8 mm.

The thickness of the layers of the porous zirconia dental mill blank may be equal or different.

According to one embodiment, the bottom layer (body area) of the porous zirconia dental mill blank is thicker than the top layer (enamel area). Such an arrangement can help to even further improve the esthetic result.

According to one embodiment, the thickness of the individual layers is as follows: bottom layer>top layer>intermediate layer(s).

An example of a dental mill blank with 6 layers is shown in FIG. 1. The values given are the layer height in mm in the pre-sintered blank.

The dental mill blank shows a color gradient from the bottom layer to the top layer. The given numbers describe the layer thickness in mm (left: powder height in the mold prior to pressing the zirconia powders; right: estimated layer height after pressing the zirconia powders).

The yttria concentration difference between adjacent layers is typically not more than 0.5 mol %, preferably in a range of 0.35 to 0.5 mol %.

This can be advantageous as the difference on the one hand is sufficiently high to obtain a measurable translucency gradient and on the other hand is sufficiently low to reduce the risk of distortion during sintering.

Further, if the difference of yttria concentration between the adjacent layers is not too high, opaque optical effects at the layer-interfaces can be avoided.

The amount of yttria and the amount of the coloring ions (given in mol %) change in opposite direction to each other from the bottom layer to the top layer of the porous zirconia dental mill blank.

According to one embodiment, the amount of yttria in the bottom layer is lower than in the top layer and the amount of coloring ions in the bottom layer is higher than in the top layer.

Thus, after sintering the dental mill blank or dental articles machined thereof shows a translucency and/or color gradient.

The amounts of yttria and coloring ions are adjusted to provide an essentially constant ratio of dopants between the top layer and bottom layer for the dental mill blanks contained in the set.

More precisely, the ratio of the sum of yttria and coloring ions in mol % between the top layer and the bottom layer of the porous zirconia dental mill blanks is essentially constant for different colors of the dental mill blanks.

Essentially constant means that the ratio of the sum of yttria and coloring ions in mol % between the top layer and the bottom layer of the porous zirconia dental mill blanks varies by a deviation D that is not more than 2.70 for all colored mill blanks of the set.

The deviation D can be calculated for each color from the ratio R mentioned above by using formula (1).

$$D_n = ((R_{max} - R_n)/R_{max} * 100) R_{max}^2 \qquad (1)$$

The set of blanks contains N colors with N≥2, n=1, 2, ..., N.

R=(amount of yttria+coloring oxides in mol % in the top layer)/(amount of yttria+coloring oxides in mol % in the bottom layer). $R_{max}$ is the highest ratio found for a color composition within the set. Usually, the highest ratio is found for the lightest color of the set.

Depending on the amount of yttria being present in the dental mill blank, the ratio of amount of yttria plus the amount of coloring ions in the top layer (in mol %) divided by the amount of yttria plus the amount of coloring ions in the bottom layer (in mol %) will vary.

E.g. for a porous zirconia dental mill blank having an yttria gradient from 3.0 to 5.5 mol % from the bottom layer to the top layer, the ratio is typically 1.83 or lower for darker colors, in particular for increasingly darker colors, preferably in a range of 1.83 to 1.67.

For a porous zirconia dental mill blank having an yttria gradient from 4.0 to 5.5 mol % from the bottom layer to the top layer, the ratio is typically 1.37 or lower for darker colors, in particular for increasingly darker colors, preferably in a range of 1.37 to 1.31.

For a porous zirconia dental mill blank having an yttria gradient from 3.0 to 5.0 mol % from the bottom layer to the top layer, the ratio is typically 1.66 or lower for darker colors, in particular for increasingly darker colors, preferably in a range of 1.66 to 1.54.

For a porous zirconia dental mill blank having an yttria gradient from 4.0 to 5.0 mol % from the bottom layer to the top layer, the ratio is typically 1.25 or lower for darker colors, in particular for increasingly darker colors, preferably in a range of 1.25 to 1.20.

For a porous zirconia dental mill blank having an yttria gradient from 3.2 to 5.65 mol % from the bottom layer to the top layer, the ratio is typically 1.76 or lower for darker colors, in particular for increasingly darker colors, preferably in a range of 1.76 to 1.62.

These differences are accounted for by formula (1). A simple way to calculate the deviation between $R_a$ and $R_{max}$ would be $(R_{max}-R_n)/R_{max}*100$, which is the deviation in percent. By division of this term by $R_{max}^2$, the result is being normalized and becomes valid for many different yttria gradients, while the more simply calculated deviation would increase with increasing yttria gradients or $R_{max}$ values, respectively.

It also has to be considered that the $R_{max}$ values given above are applicable, if the set of dental mill blanks contains very light colors and the doping with coloring ions is low. If this is not the case, the $R_{max}$ value can be lower, even if the yttria gradient is comparatively high.

The porous zirconia dental mill blank described in the present text comprises or essentially consists of or consists of zirconia, yttria and coloring ions and optionally fluorescing components and/or alumina.

The layers of the porous zirconia dental mill blank contain different amounts of yttria, typically yttria in amounts ranging from 2.8 to 7.0 mol % or 3.0 to 5.5 mol %.

The layers of the porous zirconia dental mill blank of the set of mill blanks described in the present text also contain coloring ions, in particular Er and at least one further coloring ion selected from Fe, Tb, V, Mn, Cr, Co.

Optionally, alumina can be present. If alumina is present, it is typically present in an amount up to 0.15 mol % or up to 0.1 mol % or up to 0.05 mol % with respect to the material of the porous zirconia dental mill blank.

If desired, the porous dental zirconia mill blank may also contain a fluorescing agent, in particular a Bi component. If a Bi component is present, the presence of an Fe component should be avoided.

If a Bi component is present, the Bi component (calculated as $Bi_2O_3$) is typically present in an amount up to 0.04 mol % or up to 0.03 mol % or up to 0.02 mol % with respect to the material of the porous zirconia dental mill blank.

Without wishing to be bound to a certain theory, it is believed that by using Fe as coloring agent, either the UV light needed to initiate the fluorescence or the emitted blue fluorescence light itself or even both are being absorbed by the Fe component and thus lost for the desired visual appearance.

The porous zirconia dental mill blanks of the set of dental mill blanks described in the present text typically comprise or essentially consist of $ZrO_2$ from 89.35 to 97.18 mol %, $HfO_2$ from 0 to mol %, $Y_2O_3$ from 2.8 to 7.0 mol. %, $Al_2O_3$ from 0 to 0.15 mol %, coloring ions calculated as their respective oxides from 0.02 to 0.5 mol %, mol % with respect to the chemical composition of the porous zirconia dental mill blank, the coloring ions being ions of Er and at least one further ion selected from the list of Fe, Tb, V, Mn, Cr, Co.

The amount of yttria from 2.8 to 7.0 mol % refers to each individual layer of the individual block, provided that the block has the yttria gradient described in the present text.

The porous zirconia dental mill blank can typically be characterized by the following parameters alone or in combination:
 a) average primary particle size: less than 900 nm or less than 800 nm or less than 600 nm;
 b) average connected pore diameter: 10 to 200 nm;
 c) BET surface: 2 to 20 $m^2/g$ or 5 to 16 $m^2/g$ or 7 to 14 $m^2/g$;
 d) biaxial flexural strength: 8 to 80 or 15 to 55 MPa;
 e) Vickers hardness: 25 to 150 (HV 0.5) or 35 to 140 (HV 1).

According to one embodiment, the porous zirconia dental mill blank may be characterized by the following parameters alone or in combination:
 a) average primary particle size: less than 800 nm;
 b) average connected pore diameter: 10 to 200 nm;
 c) BET surface: 2 to 20 $m^2/g$;
 d) biaxial flexural strength: 8 to 80 MPa;
 e) Vickers hardness: 25 to 150 (HV 0.5).

According to another embodiment, the porous zirconia dental mill blank may be characterized by the following parameters alone or in combination:
 a) average primary particle size: less than 600 nm;
 b) average connected pore diameter: 10 to 200 nm;
 c) BET surface: 7 to 14 $m^2/g$;
 d) biaxial flexural strength: 15 to 55 MPa;
 e) Vickers hardness: 35 to 140 (HV 1).

If desired, the respective properties can be determined as described in the example section. A combination of the parameters a) and b); or a) and c); or a) and d); or a), c) and d) can sometimes be preferred.

It was found that it can be beneficial for certain properties, if the porous zirconia material has a certain BET surface. The BET surface should be in a particular range. It should not be too small and also not be too large.

If the BET surface of the material is too low, it might not be sinter-active enough to reach or to get close to theoretical density during a speed-sintering cycle, which would negatively affect the material strength and translucency.

If the BET surface of the material is too high, it might be difficult to have sufficient control over the sintering behaviour. In this case, it would also be difficult to obtain a material of desired strength and translucency.

The Vickers hardness of the material is typically also in a particular range.

If the Vickers hardness of the material is too low, the machinability could fall off in quality (edge chipping or breaking of the workpiece) or similar difficulties with manual reworking to individualize the frame of a dental restoration or a monolithic restoration could arise as well.

If the Vickers hardness of the material is too high, the wear of the machining tools may increase to an uneconomic range or the tool could break and destroy the workpiece.

The biaxial flexural strength of the material is typically also in a particular range.

It was found that if the biaxial flexural strength of the material is too low, the material tends to crack during the milling process or during the manual finishing by a dental technician.

On the other hand, if the biaxial flexural strength of the material is too high, the processing of the material by a milling machine is often not possible with reasonable effort. The milling tool or the milled material often tend to chip or break. In such a case the shaping of the material would have to be done by grinding, e.g. using a Cerec™ grinding machine (Sirona).

It was found that a porous dental material having the above described features typically exhibits better machinability and faster sinterability compared to other commercially available dental mill blanks, while maintaining good translucency and strength.

Thus, the porous zirconia material of the porous dental zirconia mill blank described in the present text may have a unique combination of features, which facilitates a reliable production of highly aesthetic dental ceramic articles.

The porous zirconia dental mill blank may also be characterized by its shape and/or size.

The porous zirconia dental mill blank has a shape allowing the dental mill blank to be reversibly attached or fixed to a machining device. Suitable shapes include discs or blocks (e.g. cubic, cuboid, cylinder, etc.).

For a cubic or cuboid shaped dental mill blank, typical dimensions are at least 19 mm in 2 dimensions, and at least 12 mm in the third dimension.

Alternatively, the dental mill blank having the shape of a block may have the following dimensions: x-dimension: 12 to 45 mm, or 19 to 40 mm; y-dimension: 12 to 70 mm, or 19 to 60 mm; z-dimension: 10 to 40 mm, or 12 to 25 mm.

For a cylindric or disc shaped dental mill blank, typical dimensions are more than 19 mm in diameter, more than 12 mm in height.

Alternatively, a dental mill blank having the shape of a disc may have the following dimensions: x, y-dimension: 90 to 110 mm, or 95 to 105 mm; z-dimension: 10 to 35 mm, or 12 to 30 mm.

The dental mill blank may also comprise means for attaching the dental mill blank to a machining device. Suitable means include frame(s), notch(es), stub(s), mandrels and combinations thereof.

Fixing of the dental mill blank to such a means can be affected by clamping, gluing, screwing and combinations thereof. Using such a means may facilitate the production of the dental restoration with a machining device.

Examples of holding devices or means are described e.g. in U.S. Pat. No. 8,141,217 B2 (Gubler et al.), WO 02/45614 A1 (ETH Zurich), DE 203 16 004 U1 (Stuehrenberg), U.S. Pat. No. 7,985,119 B2 (Basler et al.) or WO 01/13862 (3M). The content of these documents with respect to the description of the holding device is herewith incorporated by reference.

The invention is also directed to a process of producing the set of porous dental zirconia mill blanks.

Generally, the porous zirconia material of the dental mill blank can be obtained by a process comprising the steps of
mixing powders of different compositions to obtain a powder mixture,
pressing the powder mixture,
and optionally heat-treating the pressed powder mixture.
The individual powders can be obtained by a process comprising the steps of
treating a zirconia powder with a solution containing coloring ions, in particular Er ions and further ions selected from Fe, Tb, V, Mn, Cr and/or Co,
drying the mixture to obtain a powder.
Alternatively, the individual powders can be obtained by a process comprising the steps of
treating a zirconia powder with powder containing coloring oxides, in particular a powder comprising Er oxides and further oxides of Fe, Tb, V, Mn, Cr and/or Co,
milling the mixture in wet state,
(spray-)drying the mixture to obtain a powder.

Suitable zirconia powders are commercially available from various sources including Tosoh Company (Japan).

Mixing of the individual powders can be achieved by shaking the powders or putting the powders in a mill (e.g. ball mill, attritor mill) and milling the powders until a homogenous powder mixture is obtained. Further possible mixing equipment can include sieves or granulators.

To facilitate the pressing or compacting step(s), pressing aids can be added, if desired.

Suitable pressing aids include binders, lubricating additives and mixtures thereof.

If desired, these aids can be added to the zirconia oxide powder being the main component of the powder mixture.

The powder mixture is then placed in a mould (layer-by-layer) and pressed into the shape of a dental mill blank.

The pressure to be applied is typically in the range of 150 to 300 MPa. Alternatively, the applied pressure is set so that the pressed ceramic body reaches a certain density, e.g. in the case of zirconia ceramic a density of 2.8 $g/cm^3$ to 3.5 $g/cm^3$.

In a further step, a heat treatment is typically applied to the compacted composition to obtain a porous dental mill blank. During this step, organic compounds (e.g. binder components) are removed (often referred to as calcination).

The temperature of the heat treatment is typically in a range of 800 to 1,100° C. or 900 to 1,000° C. The heat treatment is typically applied for a duration of 10 to 70 h or 15 to 60 h.

The article obtained after heat treatment can be machined or sectioned into any desired shape.

More specifically, the porous zirconia dental mill blanks of the set described in the present text can be produced by a process comprises the following steps:
providing at least the following powder compositions:
zirconia powder ZP1 having an yttria content Y1,
zirconia powder ZP2 having an yttria content Y2,
zirconia powder ZP3 containing coloring ions CI-A,
zirconia powder ZP4 containing coloring ions CI-B,
the yttria content Y2 in mol % being higher than the yttria content Y1, mixing the zirconia powders ZP1, ZP2, ZP3, and ZP4 with different mixing ratios to obtain at least
a zirconia powder composition ZP-MX-B,
a zirconia powder composition ZP-MX-$I_m$,
a zirconia powder composition ZP-MX-T,
the yttria content in mol % of the zirconia powder compositions being ZP-MX-B<ZP-MX-$I_m$<ZP-MX-T, the number of intermediate layers being M>1 with m=1, ..., M,
for each colored porous zirconia dental mill blank of the set layering the zirconia powder compositions in the cavity of a mould so that
the layer of ZP-MX-B is located below the layer of ZP-MX-$I_m$,
the layer of ZP-MX-$I_m$ is located below the layer of ZP-MX-T
compacting the layered zirconia powder compositions,
optionally heat-treating the compacted zirconia powder compositions.

According to one embodiment, the layer thickness of the zirconia powder composition layers is as follows: ZP-MX-B>ZP-MX-$I_m$<ZP-MX-T, wherein typically ZP-MX-B>ZP-MX-T.

According to one embodiment the set of porous zirconia dental mill blanks described in the present text comprising at least two differently colored porous zirconia dental mill blanks,
the porous zirconia dental mill blanks
comprising zirconia, yttria, coloring ions, and optionally alumina,
the coloring ions being selected from Er and at least one further ion selected from Fe, Tb, V, Mn, Cr, Co,
comprising 3 to 7 layers,
the first layer being referred to as bottom layer and the last layer being referred to as top layer,
the bottom layer being thicker than the top layer,
each layer having a different yttria content,
the yttria content being in a range of 2.8 to 7.0 mol % relating to the material of the porous zirconia dental mill blank,
the yttria content differing from layer to layer by not more than 0.5 mol %,
the content yttria and coloring ions in mol % changing in opposite direction to each other from the bottom layer to the top layer,
the deviation D, calculated from the ratio R of the sum of yttria and coloring ions in mol % between the top layer and the bottom layer with the formula $D_n = ((R_{max} - R_n)/R_{max} * 100)/R_{max}^2$, being not more than 2.70 for all the differently colored porous zirconia dental mill blanks within the set containing N (N≥2, n=1, 2, ..., N) different colors with $R_{max}$ being the highest ratio found within the set.

The invention is also directed to a process of producing a dental restoration from a porous zirconia dental mill blank of the set of dental mill blanks described in the present text.
Such a process typically comprises the steps of:
providing the set of porous zirconia dental mill blanks as described in the present text,
optionally determining the tooth colour of the tooth to be restored,
selecting from the set a porous zirconia dental mill blank,
machining a porous dental restoration precursor from the porous zirconia dental mill blank,
sintering the porous dental restoration precursor.

The step of selecting or choosing a porous zirconia dental mill blank is not particularly limited. Any porous zirconia dental mill blank of the set can be selected. Typically, the practitioner will select that porous zirconia dental mill blank from the set which after sintering is best suited for matching with the tooth colour of the tooth which is to be restored.

If desired, the tooth colour can be determined with a commercially available shade guide (e.g. from Vita company).

The machining step is typically done with or by using a milling or grinding device. Those devices are commercially available e.g. from Roland (DWX mills), or Sirona (CEREC™ in Lab CAD/CAM) or others.

The machining step can be done with a milling, drilling, cutting, carving, or grinding device.

Useful milling parameters include: rotary speed of milling tool: 5,000 to 40,000 revolutions/min; feed rate: 20 to 5,000 mm/min; milling cutter diameter: 0.8 to 4 mm.

If desired, the machined porous dental zirconia restoration is cleaned, e.g. by removing milling dust with pressurized air.

The process of producing the dental restoration comprises a sintering step.

The sintering will result in a zirconia dental article, sometimes also referred to as crystalline metal oxide article.

If conducted, the firing or sintering step should be accomplished under conditions which results in a dental ceramic article having an acceptable tooth-like color (e.g. a color which fits the Vita™ Classical shade system).

Useful sintering conditions can generally be characterized by the following parameters alone or in combination: temperature: 1,100 to 1,600° C. or 1,100 to 1,500° C. or 1,100° C. to 1,450° C. or 1,100° C. to 1,300° C. or 1,300° C. to 1,600° C. or 1,400° C. to 1,580° C. or 1,450° C. to 1,580° C.;
atmosphere: air;
duration: until a density of at least 98 or 99 to 100% of the theoretically achievable density of the material has been reached;
dwell time: 0 to 24 h or 0.1 to 5 h;
pressure: ambient pressure.

According to one embodiment, the sintering conditions are characterized as follows: temperature: 1,100 to 1,600° C.; atmosphere: air; duration: until a density of at least 98% of the theoretically achievable density of the material has been reached; dwell time: 0 to 24 h.

During the firing process the porous dental article is sintered to its final shape, thereby undergoing changes with regard to dimension, density, hardness, bending strength and/or grain size.

The dwell time is the time during which the article is kept at the maximum sintering temperature. The dwell time can be zero. The dwell time, however, can also be in a range of 0 to 24 h or 0.1 to 5 h.

The sintering temperature and dwell time are, however, typically correlated. A higher temperature typically requires a shorter dwell time.

Thus, the dwell time, may last from 0 to 5 h (e.g. if the firing temperature is 1,550° C.) or from 0.1 to 24 h (e.g. if the firing temperature is 1,100° C.).

Generally, the sintering or firing conditions are adjusted such that the sintered dental ceramic article has a density of equal or greater than 98% compared with the theoretically achievable density.

If a faster processing is desired, higher heating rates can be used.

Generally, useful heat-treating conditions for so-called speed or fast sintering can be characterized by the following features alone or in combination:
a) heating rate: 1.5 to 7° C./sec or 2 to 7° C./sec or 3 to 7° C./sec;
b) sintering temperature: at least 1,400° C. or at least 1,450° C. or at least 1,500° C.;
c) atmosphere: air;
d) duration: less than 60 min;
e) dwell time: 0 to 10 min;
f) pressure: ambient pressure.

According to one embodiment suitable heat-treating conditions are characterized by the following features alone or in combination:
a) heating rate: 2 to 7° C./sec;
b) sintering temperature: at least 1,500° C.;
c) atmosphere: air;
d) duration: less than 60 min;
e) dwell time: 0 to 10 min;
f) pressure: ambient pressure.

A combination of the following features is sometimes preferred: a) and b); a), b) and d); a), b), c), d) and e).

An oven which can be used for the process described in the present text is commercially available from Dentsply Sirona (SpeedFire™).

A suitable furnace is also described in WO 2017/144644 A1 (Sirona). This furnace is for carrying out a heat treatment of a dental replacement part and comprises an induction coil, a radiant heater, an insulation layer and a furnace chamber. Further, the furnace has a cooling system to control the internal temperature of the furnace chamber.

As an alternative to the fast heat treatment process where high heating rates are used, the sintering process can also be conducted by using lower heating rates.

A respective sintering protocol can be characterized as follows: heating rate: 1 to 60° C./min;
sintering temperature: 1,100 to 1,600° C.; duration: 60 to 480 min.

A furnace which can be used is the commercially available Lava™ Furnace 200 (3M Oral Care).

Described is also a dental restoration precursor which is obtained or obtainable (e.g. by applying a machining step) from the porous zirconia mill blank of the set described in the present text.

Such a dental restoration precursor or the later dental restoration obtained by sintering such a dental restoration precursor has typically the shape of an inlay, onlay, veneer, facing, coping, crown, bridge, implant, abutment, orthodontic appliances or a part thereof.

Described is also a dental restoration being obtained or being obtainable by sintering the dental restoration precursor.

Such a dental restoration is typically characterized by the following features alone or in combination:
density: 5.8 to 6.1 g/cm$^3$;
translucency: at least 30%, measured in reflection mode, averaged over a wavelength of 400 to 700 nm determined on a sample having a thickness of 1 mm and being cut from the top layer of the dental zirconia mill blank;
translucency: at least 15%, measured in reflection mode, averaged over a wavelength of 400 to 700 nm determined on a sample having a thickness of 1 mm and being cut from the bottom layer of the dental zirconia mill blank.

If desired, a sintered sample of the dental mill blank can also be characterized by further parameters, such as biaxial flexural strength and crystal phase content.

The biaxial flexural strength is typically in a range of 500 MPa to 2,000 MPa.

The crystal phase content is typically in a range of 30 to 80 wt. % for the tetragonal phase and 20 to 70 wt. % for the cubic phase.

The invention is also directed to a kit of parts. The kit of parts comprises the set of porous zirconia dental mill blanks as described in the present text, and a dental cement.

The dental cement is used for attaching or fixing a dental restoration machined out of the dental mill blank to a tooth surface.

Suitable dental cements include resin-modified glass ionomer cements (RM-GIZ) and also self-adhesive resin cements.

RM-GIZ cements typically contain an acid-reactive filler (such as a fluoro aluminosilicate glass), water, optionally polyacid, polymerizable components (such as (meth)acrylate components) and an initiator system.

Self-adhesive resin cements typically contain an acidic polymerizable component (e.g. a (meth)acrylate component bearing a phosphoric or carboxylic acid moiety), polymerizable components without an acidic moiety, an initiator system and filler.

Suitable dental cements are also commercially available, such as RelyX™ Unicem 2 or RelyX™ Luting Plus (3M Oral Care).

The kit of parts described in the present text may further comprise the following components alone or in combination: instruction for use; sintering furnace.

The instruction for use typically contains information on machining processes and parameters to be applied as well as sintering conditions useful for sintering the machined article to final density as described in the present text.

The sintering furnace can be a furnace for conducting a regular sintering process or for conducting a speed-sintering process.

Sintering devices as described in the present text can be used. Sintering furnaces are also commercially available, e.g. from 3M Oral Care, DentsplySirona, or Ivoclar.

All components used for producing the dental zirconia mill blank described in the present text should be sufficiently biocompatible, that is, the material of the dental zirconia mill blank should not produce a toxic, injurious, or immunological response in living tissue.

The dental articles described in the present text do typically not contain components or additives which jeopardize the intended purpose to be achieved with the invention. Thus, components or additives added in an amount which finally results in a non-tooth-colored dental article are usually not contained in the dental article. Typically, an article is characterized as not being tooth colored if it cannot be assigned a color from the Vita™ color code system, known to the person skilled in the art. Additionally, components which will reduce the mechanical strength of the dental restoration to a degree, where mechanical failure will occur, are usually also not included in the dental article.

Further, the producing of the zirconia dental mill blank or the dental articles obtained therefrom do typically not require the application of a hot isostatic pressing step (HIP).

More precisely, the dental mill blanks of the set described in the present text typically do not contain the following components alone or in combination: glass in an amount of more than 1 wt. %; glass ceramic in an amount of more than 1 wt. %; Ca or Mg as stabilizer in an amount of more than 1 wt. %; fluoride in an amount of more than 0.1 wt. %, wt. % with respect to the dental zirconia mill blank.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope thereof.

The following examples are given to illustrate the invention.

EXAMPLES

Unless otherwise indicated, all parts and percentages are on a weight basis, all water is de-ionized water, and all molecular weights are weight average molecular weight. Moreover, unless otherwise indicated all experiments were conducted at ambient conditions (23° C.; 1013 mbar).

Methods

Elemental Composition

If desired, the elemental composition can be determined by X-ray fluorescence spectrometry (XRF), e.g. with the ZSX Primus II from Rigaku, Japan. This method is especially suited for the analysis of solids, e.g. zirconia ceramics or glass materials.

Average Connected Pore Diameter

If desired, the average connected pore diameter can be determined as follows: Mercury is introduced in the porous material under high pressure using a porosimeter (Quantachrome Poremaster). The applied pressure is related to pore size by the opposing force of the surface tension of Mercury. Using the so-called Washburn equation, the average connected pore diameter can be determined. The following measurement parameters are applied or used for result calculation: Pressure range from 20 to 60000 PSIA, temperature during measurement 20° C., Hg Contact Angle 140° and Hg Surface Tension 480 mN/m.

Porosity

If desired, the porosity can be determined as follows: Porosity=(1−(density of porous material/density of sintered material))×100. The density of the porous material can be calculated by the division of weight and volume. Volume can be obtained by geometrical measurements.

Average Grain Size of Sintered Body

If desired, the average grain size can be determined with the Line Intercept Analysis. FESEM micrographs with 70,000 times magnification are used for grain size measurement. Three or four micrographs taken from different areas of the sintered body are used for each sample. Ten horizontal lines, which are spaced at roughly equal intervals across the height of each micrograph, are drawn. The numbers of grain boundary intercepts observed on each line are counted and used to calculate the average distance between intercepts. The average distance for each line is multiplied by 1.56 to determine the grain size and this value is averaged over all the lines for all micrographs of each sample.

Average Primary Particle Size of Powder Composition

If desired, the average primary particle size of the particles of the zirconia powders can be determined by light scattering techniques, e.g. with a Mastersizer 3000 from Malvern Panalytical.

Biaxial Flexural Strength

If desired, the biaxial flexural strength of pre-sintered material can be determined according to ISO 6872 with the following modifications: The pre-sintered sample is sawn into wafers with a thickness of 2+/−0.1 mm using a dry cut saw. The diameter of the samples should be 17+/−2 mm. The parallel large faces of the wafer are ground using silicon carbide sand paper (P2500). Each wafer is centred on a support of three steel balls (diameter of the balls 6 mm) with a support diameter of 14 mm. The punch diameter in contact with the wafer is 3.6 mm. The punch is pushed onto the wafer at a rate of 0.1 mm per min. A minimum of 15 samples is measured to determine the average strength. The tests can be conducted in an Instron 5566 universal testing machine (Instron Deutschland GmbH).

Vickers Hardness

If desired, the Vickers hardness can be determined according to ISO 14705 with the following modifications: The surface of the pre-sintered samples is ground using silicon carbide sandpaper (P2500). The surface of the sintered samples is polished with 20 µm diamond suspension. The test forces are adjusted to the hardness level of samples. Used test forces are between 0.2 kg and 2 kg and are applied for 15 s each indentation. A minimum of 10 indentations is measured to determine the average Vickers hardness. The tests can be conducted with a hardness tester Leco M-400-G (Leco Instrumente GmbH).

Density

If desired, the density of the sintered material can be measured by an Archimedes technique. The measurement is made on a precision balance using a density determination kit (identified as "YDK01" from Sartorius AG). In this procedure, the sample is first weighed in air (A), then immersed in a solution (B). The solution is a 0.05 wt. % tenside solution (e.g. "Berol 266, Fa. Hoesch) in de-ionized water. The density is calculated using the formula $\rho=(A/(A-B))\rho 0$, where $\rho 0$ is the density of water. The relative density can be calculated by reference to the theoretical density ($\rho t$) of the material, $\rho_{rel}=(\rho/\rho t)100$.

Crystalline Phase Content

If desired, the phase content can be determined by x-ray diffraction (XRD) using a Bruker D8 Discover device (Bruker AXS) and the TOPAS™ software provided by the manufacturer (Bruker) applying the Rietveld analyses and using the Bragg-Brentano geometry. The phase content calculated by the TOPAS™ software is given in wt. %. The measurement is typically performed down to a depth of 3 to 6 μm, which is approximately the penetration depth of x-rays in zirconia.

BET Surface

If desired, the BET surface of a porous article can be determined as follows: Total pore volume and average pore diameter can be analyzed with the use of $N_2$ sorption isotherms and BET surface area analysis. Samples of around 0.1-2 grams were cut, if necessary, from larger samples in order to be inserted into the straight testing tubes of the instrument. All samples are degassed in vacuum for more than 1 h at 120° C. before analysis. The samples are then analyzed by adsorption and desorption of $N_2$ gas with a Belsorb II (distributed by Robotherm Präzisionsmesstechnik, Bochum, Germany) in a 9 mm cell with 2 cm bulb and with a 5 mm glass rod. At temperature of liquid nitrogen, absorption data points are collected from 0.1 to 0.99 p/p0 and desorption points collected from 0.99 to 0.5 p/p0. The specific surface area S is calculated by the BET method at p/p0 0.25-0.3 (Details regarding calculation see Belsorb Analysis Software User Manual Operating Manual, Chapter 12, Bel Japan. INC).

Fluorescence

If desired, the samples are placed in an UV-light box used for inspection of e.g. thin layer chromatography plates. Fluorescence can be detected by the human eye by the lighting up of the sample against the black background.

Method for Measuring Translucency

If desired, the translucency of the ceramic articles can be evaluated with the following procedure: A test piece in the shape of a disc with an approximate thickness of 1±0.05 mm and an area of measurement of at least 10 mm in diameter is provided. For preparation of the test pieces a pre-sintered block-shaped sample is sawn into wafers with a thickness of approximately 1.3 mm using a dry cut saw. The parallel large faces of the wafer are ground using silicon carbide sandpaper (P2500). Alternatively, disc-shaped samples can also be produced during the pressing step, which eliminates the need for sawing and grinding. The samples are sintered in an appropriate furnace to a sintered sample with a thickness of 1±0.05 mm. The sintered sample is measured as fired with a spectrophotometer (e.g. X-Rite Color i7, Grand Rapids, USA) in reflectance mode against a white and a black background to obtain the opacity (contrast ratio) of the material, which is an average value over the wavelengths from 400 to 700 nm. The translucency T is calculated according to T=100%–opacity (in percent). Higher values of translucency are indicative of greater transmission of light, and less opacity.

Color

If desired, L*a*b* values can be determined using the same equipment and material samples which are used for determining the opacity (contrast ratio) and translucency.

Materials

The powders described in Table 1 can be used:

TABLE 1

Amounts of inorganic components in zirconia powders used in the examples (in mol %).

| | |
|---|---|
| ZRO2-3.2Y | Bindered yttrium oxide containing zirconia powder<br>$ZrO_2$: 95.4724 mol %; $HfO_2$: 1.2117 mol %; $Y_2O_3$: 3.1908 mol %; $Al_2O_3$: 0.1251 mol % |
| ZRO2-4.0Y | Bindered yttrium oxide containing zirconia powder<br>$ZrO_2$: 94.6478 mol %; $HfO_2$: 1.2200 mol %; $Y_2O_3$: 4.0315 mol %; $Al_2O_3$: 0.1007 mol % |
| ZRO2-5.6Y | Bindered yttrium oxide containing zirconia powder<br>$ZrO_2$: 92.9859 mol %; $HfO_2$: 1.2359 mol %; $Y_2O_3$: 5.6506 mol %; $Al_2O_3$: 0.1276 mol % |
| ZRO2-P1 (Er) "pink" | Bindered, erbium oxide and yttrium oxide containing zirconia powder<br>$ZrO_2$: 94.1617 mol %; $HfO_2$: 1.2440 mol %; $Y_2O_3$: 3.1483 mol %; $Al_2O_3$: 0.1284 mol %; $Er_2O_3$: 1.3176 mol % |
| ZRO2-P2 (Er) "pink" | Bindered, erbium oxide containing zirconia powder<br>$ZrO_2$: 95.4606 mol %; $HfO_2$: 1.2586 mol %; $Y_2O_3$: 0.0000 mol %; $Al_2O_3$: 0.1299 mol %; $Er_2O_3$: 3.1509 mol % |
| ZRO2-Y (Tb) "yellow" | Bindered, terbium oxide and yttrium oxide containing zirconia powder<br>$ZrO_2$: 95.1115 mol %; $HfO_2$: 1.2324 mol %; $Y_2O_3$: 3.1820 mol %; $Al_2O_3$: 0.1272 mol %; $Tb4O_7$: 0.3469 mol % |
| ZRO2-G (Mn) "grey" | Bindered, manganese oxide and yttrium oxide containing zirconia powder<br>$ZrO_2$: 95.4218 mol %; $HfO_2$: 1.2115 mol %; $Y_2O_3$: 3.1903 mol %; $Al_2O_3$: 0.1251 mol %; $MnO_2$: 0.0513 mol % |

The molecular weights used for the calculations are: $ZrO_2$: 123.22 g/mol; $HfO_2$: 210.49 g/mol; $Y_2O_3$: 225.81 g/mol; $Al_2O_3$: 101.96 g/mol; $Er_2O_3$: 382.56 g/mol; $Tb4O_7$: 747.70 g/mol; $MnO_2$: 86.94 g/mol.

General Procedure for Producing Individual Zirconia Powders

The individual powders can be obtained by a process comprising the steps of treating a co-precipitated zirconia/hafnia/yttria powder with powder containing coloring oxides, for the examples with oxides of Er, Tb or Mn, optionally also adding alumina powder, milling the mixture in wet state and (spray-)drying the mixture to obtain a pressable powder.

General Procedure for Producing Mixed Zirconia Powders

Mixed powders can be produced by combination of four of the raw materials from Table 1 (e.g. ZRO2-3.2Y and ZRO2-P1 (Er) and ZRO2-Y (Tb) and ZRO2-G (Mn)) in the desired amounts and shaking the mixture with a lab mixing device (Minishaker MS2 from IKA) until a homogeneous mixture is obtained.

General Procedure for Producing Dental Zirconia Samples

Samples can be produced by using the above described zirconia materials.
The following steps are applied:
Mixing four of the zirconia powders to a powder composition;
Filling the powder composition in a mould (diameter: 24.9 mm);
Applying pressure (97 kN) to the powder filling;
Demoulding the compacted body;
Applying a heat treatment of 960° C. for about 1 hour;
Slicing and grinding discs from the obtained block.

The samples are of approximately 1.3 mm in thickness. After sintering, the sample dimensions are adequate for color and translucency measurements.

Inventive Example (IE) 1

Y-gradient from approx. 3.0 mol % $Y_2O_3$ in body and approx. 5.6 mol % $Y_2O_3$ in enamel: Zirconia powders ZRO2-3.2Y, ZRO2-5.6Y, ZRO2-P2, ZRO2-Y and ZRO2-G are mixed at different ratios to obtain a body composition (with ZRO2-3.2Y) and an enamel composition (with ZRO2-5.6Y) for different Vita™ Classical shades (i.e. A1, A2, A3, A4, B4, C4, D4) and a very light bleach shade.

TABLE 2a

Compositions for Inventive Example 1 (IE1).

| | IE1 Bleach Body | IE1 Bleach Enamel | IE1 A1 Body | IE1 A1 Enamel | IE1 A2 Body | IE1 A2 Enamel | IE1 A3 Body | IE1 A3 Enamel |
|---|---|---|---|---|---|---|---|---|
| ZRO2-3.2Y/wt. % | 97.0 | 0.0 | 94.5 | 0.0 | 89.0 | 0.0 | 85.0 | 0.0 |
| ZRO2-5.6Y/wt. % | 0.0 | 98.5 | 0.0 | 96.0 | 0.0 | 93.6 | 0.0 | 91.0 |
| ZRO2-P2/wt. % | 1.5 | 0.8 | 2.0 | 1.0 | 5.5 | 2.7 | 7.5 | 4.0 |
| ZRO2-Y/wt. % | 0.5 | 0.2 | 1.5 | 1.0 | 3.0 | 1.2 | 4.5 | 2.5 |
| ZRO2-G/wt. % | 1.0 | 0.5 | 2.0 | 2.0 | 2.5 | 2.5 | 3.0 | 2.5 |
| $ZrO_2$/mol % | 95.4700 | 93.0221 | 95.4659 | 93.0812 | 95.4599 | 93.1392 | 95.4540 | 93.1986 |
| $HfO_2$/mol % | 1.2125 | 1.2359 | 1.2129 | 1.2356 | 1.2148 | 1.2358 | 1.2160 | 1.2360 |
| $Y_2O_3$/mol % | 3.1446 | 5.5887 | 3.1292 | 5.5202 | 3.0211 | 5.4084 | 2.9592 | 5.3040 |
| $Al_2O_3$/mol % | 0.1252 | 0.1276 | 0.1252 | 0.1275 | 0.1254 | 0.1276 | 0.1255 | 0.1276 |
| $Er_2O_3$/mol % | 0.0455 | 0.0248 | 0.0607 | 0.0309 | 0.1673 | 0.0835 | 0.2283 | 0.1238 |
| $Tb_4O_7$/mol % | 0.0017 | 0.0007 | 0.0051 | 0.0035 | 0.0103 | 0.0042 | 0.0154 | 0.0087 |
| $MnO_2$/mol % | 0.0005 | 0.0003 | 0.0010 | 0.0010 | 0.0013 | 0.0013 | 0.0015 | 0.0013 |
| Sum Color Oxides/mol % | 0.0478 | 0.0257 | 0.0669 | 0.0355 | 0.1788 | 0.0890 | 0.2453 | 0.1338 |
| Sum Color Oxides + Yttrium Oxide/mol % | 3.1924 | 5.6145 | 3.1960 | 5.5557 | 3.1999 | 5.4974 | 3.2044 | 5.4378 |

TABLE 2b

Compositions for Inventive Example 1 (IE1) (cont.).

| | IE1 A4 Body | IE1 A4 Enamel | IE1 B4 Body | IE1 B4 Enamel | IE1 C4 Body | IE1 C4 Enamel | IE1 D4 Body | IE1 D4 Enamel |
|---|---|---|---|---|---|---|---|---|
| ZRO2-3.2Y/wt. % | 68.0 | 0.0 | 79.5 | 0.0 | 65.5 | 0.0 | 83.1 | 0.0 |
| ZRO2-5.6Y/wt. % | 0.0 | 86.0 | 0.0 | 90.0 | 0.0 | 81.0 | 0.0 | 92.6 |
| ZRO2-P2/wt. % | 12.0 | 7.0 | 5.0 | 3.5 | 9.5 | 7.5 | 1.4 | 1.4 |
| ZRO2-Y/wt. % | 10.0 | 4.0 | 8.5 | 4.0 | 9.0 | 5.5 | 6.5 | 2.0 |
| ZRO2-G/wt. % | 10.0 | 3.0 | 7.0 | 2.5 | 16.0 | 6.0 | 9.0 | 4.0 |

TABLE 2b-continued

Compositions for Inventive Example 1 (IE1) (cont.).

|  | IE1 A4 Body | IE1 A4 Enamel | IE1 B4 Body | IE1 B4 Enamel | IE1 C4 Body | IE1 C4 Enamel | IE1 D4 Body | IE1 D4 Enamel |
|---|---|---|---|---|---|---|---|---|
| $ZrO_2$/mol % | 95.4303 | 93.3160 | 95.4380 | 93.2184 | 95.4311 | 93.4345 | 95.4446 | 93.1619 |
| $HfO_2$/mol % | 1.2192 | 1.2365 | 1.2157 | 1.2359 | 1.2178 | 1.2359 | 1.2136 | 1.2351 |
| $Y_2O_3$/mol % | 2.8190 | 5.0876 | 3.0359 | 5.2947 | 2.8966 | 4.9478 | 3.1471 | 5.4232 |
| $Al_2O_3$/mol % | 0.1258 | 0.1276 | 0.1255 | 0.1276 | 0.1257 | 0.1276 | 0.1253 | 0.1275 |
| $Er_2O_3$/mol % | 0.3663 | 0.2167 | 0.1522 | 0.1083 | 0.2896 | 0.2320 | 0.0425 | 0.0433 |
| $Tb_4O_7$/mol % | 0.0343 | 0.0139 | 0.0291 | 0.0139 | 0.0309 | 0.0191 | 0.0222 | 0.0070 |
| $MnO_2$/mol % | 0.0052 | 0.0016 | 0.0036 | 0.0013 | 0.0083 | 0.0031 | 0.0046 | 0.0021 |
| Sum Color Oxides/mol % | 0.4057 | 0.2322 | 0.1849 | 0.1235 | 0.3287 | 0.2543 | 0.0694 | 0.0523 |
| Sum Color Oxides + Yttrium Oxide/mol % | 3.2247 | 5.3198 | 3.2208 | 5.4182 | 3.2254 | 5.2021 | 3.2165 | 5.4755 |

Inventive Example (IE) 2

Y-gradient from approx. 4.0 mol % $Y_2O_3$ in body and approx. 5.6 mol % $Y_2O_3$ in enamel: Zirconia powders ZRO2-4.0Y, ZRO2-5.6Y, ZRO2-P2, ZRO2-Y and ZRO2-G are used to obtain a less pronounced Y-gradient.

TABLE 3a

Compositions for Inventive Example 2 (IE2).

|  | IE2 Bleach Body | IE2 Bleach Enamel | IE2 A1 Body | IE2 A1 Enamel | IE2 A2 Body | IE2 A2 Enamel | IE2 A3 Body | IE2 A3 Enamel |
|---|---|---|---|---|---|---|---|---|
| ZRO2-4.0Y/wt. % | 97.0 | 0.0 | 94.5 | 0.0 | 89.0 | 0.0 | 85.0 | 0.0 |
| ZRO2-5.6Y/wt. % | 0.0 | 98.5 | 0.0 | 96.0 | 0.0 | 93.6 | 0.0 | 91.0 |
| ZRO2-P2/wt. % | 1.5 | 0.8 | 2.0 | 1.0 | 5.5 | 2.7 | 7.5 | 4.0 |
| ZRO2-Y/wt. % | 0.5 | 0.2 | 1.5 | 1.0 | 3.0 | 1.2 | 4.5 | 2.5 |
| ZRO2-G/wt. % | 1.0 | 0.5 | 2.0 | 2.0 | 2.5 | 2.5 | 3.0 | 2.5 |
| $ZrO_2$/mol % | 94.6697 | 93.0221 | 94.6860 | 93.0812 | 94.7245 | 93.1392 | 94.7512 | 93.1986 |
| $HfO_2$/mol % | 1.2205 | 1.2359 | 1.2208 | 1.2356 | 1.2222 | 1.2358 | 1.2231 | 1.2360 |
| $Y_2O_3$/mol % | 3.9602 | 5.5887 | 3.9237 | 5.5202 | 3.7697 | 5.4084 | 3.6742 | 5.3040 |
| $Al_2O_3$/mol % | 0.1015 | 0.1276 | 0.1022 | 0.1275 | 0.1037 | 0.1276 | 0.1048 | 0.1276 |
| $Er_2O_3$/mol% | 0.0458 | 0.0248 | 0.0611 | 0.0309 | 0.1683 | 0.0835 | 0.2297 | 0.1238 |
| $Tb_4O_7$/mol % | 0.0017 | 0.0007 | 0.0052 | 0.0035 | 0.0103 | 0.0042 | 0.0155 | 0.0087 |
| $MnO_2$/mol % | 0.0005 | 0.0003 | 0.0010 | 0.0010 | 0.0013 | 0.0013 | 0.0016 | 0.0013 |
| Sum Color Oxides/mol % | 0.0481 | 0.0257 | 0.0673 | 0.0355 | 0.1799 | 0.0890 | 0.2467 | 0.1338 |
| Sum Color Oxides + Yttrium Oxide/mol % | 4.0082 | 5.6145 | 3.9910 | 5.5557 | 3.9496 | 5.4974 | 3.9209 | 5.4378 |

TABLE 3b

Compositions for Inventive Example 2 (IE2) (cont.).

| | IE2 A4 Body | IE2 A4 Enamel | IE2 B4 Body | IE2 B4 Enamel | IE2 C4 Body | IE2 C4 Enamel | IE2 D4 Body | IE2 D4 Enamel |
|---|---|---|---|---|---|---|---|---|
| ZRO2-4.0Y/wt. % | 68.0 | 0.0 | 79.5 | 0.0 | 65.5 | 0.0 | 83.1 | 0.0 |
| ZRO2-5.6Y/wt. % | 0.0 | 86.0 | 0.0 | 90.0 | 0.0 | 81.0 | 0.0 | 92.6 |
| ZRO2-P2/wt. % | 12.0 | 7.0 | 5.0 | 3.5 | 9.5 | 7.5 | 1.4 | 1.4 |
| ZRO2-Y/wt. % | 10.0 | 4.0 | 8.5 | 4.0 | 9.0 | 5.5 | 6.5 | 2.0 |
| ZRO2-G/wt. % | 10.0 | 3.0 | 7.0 | 2.5 | 16.0 | 6.0 | 9.0 | 4.0 |
| $ZrO_2$/mol % | 94.8670 | 93.3160 | 94.7810 | 93.2184 | 94.8893 | 93.4345 | 94.7588 | 93.1619 |
| $HfO_2$/mol % | 1.2249 | 1.2365 | 1.2223 | 1.2359 | 1.2233 | 1.2359 | 1.2206 | 1.2351 |
| $Y_2O_3$/mol % | 3.3912 | 5.0876 | 3.7047 | 5.2947 | 3.4475 | 4.9478 | 3.8458 | 5.4232 |
| $Al_2O_3$/mol % | 0.1092 | 0.1276 | 0.1061 | 0.1276 | 0.1097 | 0.1276 | 0.1050 | 0.1275 |
| $Er_2O_3$/mol % | 0.3680 | 0.2167 | 0.1530 | 0.1083 | 0.2909 | 0.2320 | 0.0428 | 0.0433 |
| $Tb_4O_7$/mol % | 0.0345 | 0.0139 | 0.0292 | 0.0139 | 0.0310 | 0.0191 | 0.0223 | 0.0070 |
| $MnO_2$/mol % | 0.0052 | 0.0016 | 0.0036 | 0.0013 | 0.0083 | 0.0031 | 0.0047 | 0.0021 |
| Sum Color Oxides/mol % | 0.4076 | 0.2322 | 0.1859 | 0.1235 | 0.3302 | 0.2543 | 0.0698 | 0.0523 |
| Sum Color Oxides + Yttrium Oxide/mol % | 3.7988 | 5.3198 | 3.8906 | 5.4182 | 3.7777 | 5.2021 | 3.9156 | 5.4755 |

Comparative Example (CE) 1

Y-gradient from approx. 3.0 mol % $Y_2O_3$ in body and approx. 5.6 mol % $Y_2O_3$ in enamel:

A different erbium doped zirconia powder from Inventive Example 1 is used to obtain the same colors as in IE1. Powders ZRO2-3.2Y, ZRO2-5.6Y, ZRO2-P1, ZRO2-Y and ZRO2-G are used.

TABLE 4a

Compositions for Comparative Example 1 (CE1).

| | CE1 Bleach Body | CE1 Bleach Enamel | CE1 A1 Body | CE1 A1 Enamel | CE1 A2 Body | CE1 A2 Enamel | CE1 A3 Body | CE1 A3 Enamel |
|---|---|---|---|---|---|---|---|---|
| ZRO2-3.2Y/wt. % | 95.0 | 0.0 | 91.7 | 0.0 | 81.5 | 0.0 | 74.8 | 0.0 |
| ZRO2-5.6Y/wt. % | 0.0 | 97.4 | 0.0 | 94.6 | 0.0 | 89.9 | 0.0 | 85.5 |
| ZRO2-P1/wt. % | 3.5 | 1.9 | 4.8 | 2.4 | 13.0 | 6.4 | 17.7 | 9.5 |
| ZRO2-Y/wt. % | 0.5 | 0.2 | 1.5 | 1.0 | 3.0 | 1.2 | 4.5 | 2.5 |
| ZRO2-G/wt. % | 1.0 | 0.5 | 2.0 | 2.0 | 2.5 | 2.5 | 3.0 | 2.5 |
| $ZrO_2$/mol % | 95.4254 | 93.0248 | 95.4047 | 93.0849 | 95.2939 | 93.1484 | 95.2277 | 93.2123 |
| $HfO_2$/mol % | 1.2129 | 1.2359 | 1.2135 | 1.2355 | 1.2164 | 1.2357 | 1.2182 | 1.2359 |
| $Y_2O_3$/mol % | 3.1893 | 5.5859 | 3.1887 | 5.5161 | 3.1851 | 5.3991 | 3.1830 | 5.2898 |
| $Al_2O_3$/mol % | 0.1252 | 0.1276 | 0.1253 | 0.1275 | 0.1256 | 0.1276 | 0.1257 | 0.1276 |
| $Er_2O_3$/mol % | 0.0450 | 0.0249 | 0.0617 | 0.0314 | 0.1675 | 0.0838 | 0.2284 | 0.1244 |
| $Tb_4O_7$/mol % | 0.0017 | 0.0007 | 0.0051 | 0.0035 | 0.0103 | 0.0042 | 0.0154 | 0.0087 |
| $MnO_2$/mol % | 0.0005 | 0.0003 | 0.0010 | 0.0010 | 0.0013 | 0.0013 | 0.0015 | 0.0013 |
| Sum Color Oxides/mol % | 0.0472 | 0.0259 | 0.0678 | 0.0359 | 0.1791 | 0.0893 | 0.2453 | 0.1344 |
| Sum Color Oxides + Yttrium Oxide/mol % | 3.2365 | 5.6118 | 3.2565 | 5.5520 | 3.3642 | 5.4884 | 3.4283 | 5.4242 |

TABLE 4b

Compositions for Comparative Example 1 (CE1) (cont.).

|  | CE1 A4 Body | CE1 A4 Enamel | CE1 B4 Body | CE1 B4 Enamel | CE1 C4 Body | CE1 C4 Enamel | CE1 D4 Body | CE1 D4 Enamel |
|---|---|---|---|---|---|---|---|---|
| ZRO2-3.2Y/ wt. % | 51.5 | 0.0 | 72.6 | 0.0 | 52.5 | 0.0 | 81.2 | 0.0 |
| ZRO2-5.6Y/ wt. % | 0.0 | 76.5 | 0.0 | 85.2 | 0.0 | 70.7 | 0.0 | 90.7 |
| ZRO2-P1 / wt. % | 28.5 | 16.5 | 11.9 | 8.3 | 22.5 | 17.8 | 3.3 | 3.3 |
| ZRO2-Y/ wt. % | 10.0 | 4.0 | 8.5 | 4.0 | 9.0 | 5.5 | 6.5 | 2.0 |
| ZRO2-G/ wt. % | 10.0 | 3.0 | 7.0 | 2.5 | 16.0 | 6.0 | 9.0 | 4.0 |
| $ZrO_2$/ mol % | 95.0643 | 93.3386 | 95.2860 | 93.2302 | 95.1427 | 93.4601 | 95.4026 | 93.1664 |
| $HfO_2$/ mol % | 1.2228 | 1.2363 | 1.2172 | 1.2358 | 1.2206 | 1.2356 | 1.2140 | 1.2351 |
| $Y_2O_3$/ mol % | 3.1780 | 5.0659 | 3.1851 | 5.2826 | 3.1806 | 4.9215 | 3.1888 | 5.4188 |
| $Al_2O_3$/ mol % | 0.1262 | 0.1276 | 0.1256 | 0.1276 | 0.1260 | 0.1275 | 0.1253 | 0.1275 |
| $Er_2O_3$/ mol % | 0.3691 | 0.2161 | 0.1534 | 0.1086 | 0.2909 | 0.2330 | 0.0424 | 0.0432 |
| $Tb_4O_7$/ mol % | 0.0344 | 0.0139 | 0.0291 | 0.0139 | 0.0309 | 0.0191 | 0.0222 | 0.0070 |
| $MnO_2$/ mol % | 0.0052 | 0.0016 | 0.0036 | 0.0013 | 0.0083 | 0.0031 | 0.0046 | 0.0021 |
| Sum Color Oxides/ mol % | 0.4087 | 0.2316 | 0.1861 | 0.1238 | 0.3301 | 0.2552 | 0.0692 | 0.0523 |
| Sum Color Oxides + Yttrium Oxide/ mol % | 3.5867 | 5.2975 | 3.3712 | 5.4064 | 3.5107 | 5.1767 | 3.2580 | 5.4711 |

Comparative Example (CE) 2

Y-gradient from approx. 4.0 mol % $Y_2O_3$ in body and approx. 5.6 mol % $Y_2O_3$ in enamel:

Zirconia powders ZRO2-4.0Y, ZRO2-5.6Y, ZRO2-P1, ZRO2-Y and ZRO2-G are used to obtain a less pronounced Y-gradient.

TABLE 5a

Compositions for Comparative Example 2 (CE2).

|  | CE2 Bleach Body | CE2 Bleach Enamel | CE2 A1 Body | CE2 A1 Enamel | CE2 A2 Body | CE2 A2 Enamel | CE2 A3 Body | CE2 A3 Enamel |
|---|---|---|---|---|---|---|---|---|
| ZRO2-4.0Y/ wt. % | 95.0 | 0.0 | 91.7 | 0.0 | 81.5 | 0.0 | 74.8 | 0.0 |
| ZRO2-5.6Y/ wt. % | 0.0 | 97.4 | 0.0 | 94.6 | 0.0 | 89.9 | 0.0 | 85.5 |
| ZRO2-P1/ wt. % | 3.5 | 1.9 | 4.8 | 2.4 | 13.0 | 6.4 | 17.7 | 9.5 |
| ZRO2-Y/ wt. % | 0.5 | 0.2 | 1.5 | 1.0 | 3.0 | 1.2 | 4.5 | 2.5 |
| ZRO2-G/ wt. % | 1.0 | 0.5 | 2.0 | 2.0 | 2.5 | 2.5 | 3.0 | 2.5 |
| $ZrO_2$/ mol % | 94.6412 | 93.0248 | 94.6474 | 93.0849 | 94.6190 | 93.1484 | 94.6073 | 93.2123 |
| $HfO_2$/ mol % | 1.2208 | 1.2359 | 1.2211 | 1.2355 | 1.2232 | 1.2357 | 1.2245 | 1.2359 |
| $Y_2O_3$/ mol % | 3.9885 | 5.5859 | 3.9603 | 5.5161 | 3.8721 | 5.3991 | 3.8141 | 5.2898 |
| $Al_2O_3$/ mol % | 0.1021 | 0.1276 | 0.1029 | 0.1275 | 0.1057 | 0.1276 | 0.1075 | 0.1276 |
| $Er_2O_3$/ mol % | 0.0453 | 0.0249 | 0.0621 | 0.0314 | 0.1684 | 0.0838 | 0.2296 | 0.1244 |

TABLE 5a-continued

Compositions for Comparative Example 2 (CE2).

|  | CE2 Bleach Body | CE2 Bleach Enamel | CE2 A1 Body | CE2 A1 Enamel | CE2 A2 Body | CE2 A2 Enamel | CE2 A3 Body | CE2 A3 Enamel |
|---|---|---|---|---|---|---|---|---|
| $Tb_4O_7$/mol % | 0.0017 | 0.0007 | 0.0052 | 0.0035 | 0.0103 | 0.0042 | 0.0155 | 0.0087 |
| $MnO_2$/mol % | 0.0005 | 0.0003 | 0.0010 | 0.0010 | 0.0013 | 0.0013 | 0.0016 | 0.0013 |
| Sum Color Oxides/mol % | 0.0475 | 0.0259 | 0.0683 | 0.0359 | 0.1800 | 0.0893 | 0.2467 | 0.1344 |
| Sum Color Oxides + Yttrium Oxide/mol % | 4.0360 | 5.6118 | 4.0286 | 5.5520 | 4.0521 | 5.4884 | 4.0608 | 5.4242 |

TABLE 5b

Compositions for Comparative Example 2 (CE2) (cont.).

|  | CE2 A4 Body | CE2 A4 Enamel | CE2 B4 Body | CE2 B4 Enamel | CE2 C4 Body | CE2 C4 Enamel | CE2 D4 Body | CE2 D4 Enamel |
|---|---|---|---|---|---|---|---|---|
| ZRO2-4.0Y/wt. % | 51.5 | 0.0 | 72.6 | 0.0 | 52.5 | 0.0 | 81.2 | 0.0 |
| ZRO2-5.6Y/wt. % | 0.0 | 76.5 | 0.0 | 85.2 | 0.0 | 70.7 | 0.0 | 90.7 |
| ZRO2-P1/wt. % | 28.5 | 16.5 | 11.9 | 8.3 | 22.5 | 17.8 | 3.3 | 3.3 |
| ZRO2-Y/wt. % | 10.0 | 4.0 | 8.5 | 4.0 | 9.0 | 5.5 | 6.5 | 2.0 |
| ZRO2-G/wt. % | 10.0 | 3.0 | 7.0 | 2.5 | 16.0 | 6.0 | 9.0 | 4.0 |
| $ZrO_2$/mol % | 94.6357 | 93.3386 | 94.6847 | 93.2302 | 94.7068 | 93.4601 | 94.7321 | 93.1664 |
| $HfO_2$/mol % | 1.2271 | 1.2363 | 1.2233 | 1.2358 | 1.2251 | 1.2356 | 1.2208 | 1.2351 |
| $Y_2O_3$/mol % | 3.6134 | 5.0659 | 3.7970 | 5.2826 | 3.6237 | 4.9215 | 3.8719 | 5.4188 |
| $Al_2O_3$/mol % | 0.1136 | 0.1276 | 0.1079 | 0.1276 | 0.1132 | 0.1275 | 0.1055 | 0.1275 |
| $Er_2O_3$/mol % | 0.3704 | 0.2161 | 0.1542 | 0.1086 | 0.2919 | 0.2330 | 0.0427 | 0.0432 |
| $Tb_4O_7$/mol % | 0.0345 | 0.0139 | 0.0293 | 0.0139 | 0.0310 | 0.0191 | 0.0223 | 0.0070 |
| $MnO_2$/mol % | 0.0052 | 0.0016 | 0.0036 | 0.0013 | 0.0083 | 0.0031 | 0.0047 | 0.0021 |
| Sum Color Oxides/mol % | 0.4101 | 0.2316 | 0.1871 | 0.1238 | 0.3312 | 0.2552 | 0.0697 | 0.0523 |
| Sum Color Oxides + Yttrium Oxide/mol % | 4.0235 | 5.2975 | 3.9841 | 5.4064 | 3.9549 | 5.1767 | 3.9416 | 5.4711 |

The Inventive and Comparative Examples of each respective color were aimed to contain the same mol % of coloring ions. However, the accuracy of the amounts of different ZRO2-powders was chosen to be tenths of percent by weight. This is a reasonable accuracy to work with in a manufacturing process, but it may cause very small variations in the compositions of the mixed powders. Such small variations have negligible influence on the resulting color.

The "Ratio R Color" values shown in Table 6 are calculated from the mol % values and therefore can also sometimes be off in the last digit. The person skilled in the art will understand that the exact same compositions (down to the fourth digit in the Tables 2-5) can be obtained, if the accuracy of the amounts of different ZRO2-powders is increased to be hundredths or even thousandths of percent by weight, although this will bring no additional benefit to the material.

"Ratio R Color" is calculated by division of "Sum Color Oxides" of Enamel by "Sum Color Oxides" of Body for each color from Tables 2-5.

"Ratio R Color+Y" is calculated by division of "Sum Color Oxides+Yttrium Oxide" of Enamel by "Sum Color Oxides+Yttrium Oxide" of Body for each color from Tables 2-5.

"Deviation D Color+Y" is calculated by using formula (1) with $R_n$ being the "Ratio R Color+Y" value for the respective color and $R_{max}$ being the "Ratio R Color+Y" value for Bleach.

Values for D that exceed the limit of 2.70 are underlined.

E.g. for Inventive Example 1 (A1) the calculation is as follows:

"Sum Color Oxides (A1)" of Enamel: 0.0355 mol %
"Sum Color Oxides (A1)" of Body: 0.0669 mol %
=>"Ratio R Color (A1)": 0.0355 mol %/0.0669 mol %=0.5306
"Sum Color Oxides+Yttrium Oxide (A1)" of Enamel: 5.5557 mol %
"Sum Color Oxides+Yttrium Oxide (A1)" of Body: 3.1960 mol %
=>"Ratio R Color+Y (A1)": 5.5557 mol %/3.1960 mol %=1.7383
"Sum Color Oxides+Yttrium Oxide (Bleach)" of Enamel: 5.6145 mol %
"Sum Color Oxides+Yttrium Oxide (Bleach)" of Body: 3.1924 mol %
=>"Ratio R Color (Bleach)": 5.6145 mol %/3.1924 mol %=1.7587
"$R_{max}$" corresponds to "Ratio R Color Y (Bleach)": 1.7587
"$R_{A1}$" corresponds to "Ratio R Color Y (A1)": 1.7383
=>$D_{A1}=((R_{max}-R_{A1})/R_{max}*100)/R_{max}^2=((1.7587-1.7383)/1.7587*100)/1.7587^2=((0.0204/1.7587)*100)/3.0930=1.1604/3.0930=0.3751$ The Inventive Examples with their high and stable "Ratio R Color+Y" values are expected to show a desirable, pronounced and reliable translucency gradient over a wide range of different colors.

The invention claimed is:

1. A set of porous zirconia dental mill blanks comprising at least two differently colored porous zirconia dental mill blanks,
   the porous zirconia dental mill blanks
       comprising zirconia, yttria, coloring ions, and optionally alumina,
       comprising multiple layers with different yttria content, having a bottom layer, at least one intermediate layer, and a top layer,
       the content of yttria and coloring ions in mol % changing in opposite direction to each other from the bottom layer to the top layer, and
       wherein the multiple layers comprise a gradient in yttria and coloring ion content, with the content of yttria and coloring ions changing in opposite directions from the bottom layer to the top layer, wherein each layer differs in the content of yttria by not more than 0.5 mol % relative to a respective adjacent layer in the multiple layers,
   the content of yttria and coloring ions in mol % being adjusted to provide an essentially constant ratio of the sum of yttria and coloring ions in mol % between the top layer and the bottom layer for the differently colored zirconia dental mill blanks, the essentially

TABLE 6

Calculated Ratios R Color, Ratios R Color + Y and Deviations D Color + Y.

| | IE1 | | | IE2 | | | CE1 | | | CE2 | | |
| --- | --- | --- | --- | --- | --- | --- | --- | --- | --- | --- | --- | --- |
| | Ratio R Color | Ratio R Color + Y | Deviation D Color + Y | Ratio R Color | Ratio R Color + Y | Deviation D Color + Y | Ratio R Color | Ratio R Color + Y | Deviation D Color + Y | Ratio R Color | Ratio R Color + Y | Deviation D Color + Y |
| Bleach | 0.54 | 1.76 | 0.00 | 0.53 | 1.40 | 0.00 | 0.55 | 1.73 | 0.00 | 0.54 | 1.39 | 0.00 |
| A1 | 0.53 | 1.74 | 0.38 | 0.53 | 1.39 | 0.32 | 0.53 | 1.70 | 0.56 | 0.53 | 1.38 | 0.46 |
| A2 | 0.50 | 1.72 | 0.75 | 0.49 | 1.39 | 0.32 | 0.50 | 1.63 | 1.97 | 0.50 | 1.35 | 1.34 |
| A3 | 0.55 | 1.70 | 1.14 | 0.54 | 1.39 | 0.50 | 0.55 | 1.58 | 2.91 | 0.54 | 1.34 | 2.03 |
| A4 | 0.57 | 1.65 | 2.00 | 0.57 | 1.40 | 0.01 | 0.57 | 1.48 | 4.93 | 0.56 | 1.32 | 2.75 |
| B4 | 0.67 | 1.68 | 1.41 | 0.66 | 1.39 | 0.29 | 0.67 | 1.60 | 2.50 | 0.66 | 1.36 | 1.24 |
| C4 | 0.77 | 1.61 | 2.68 | 0.77 | 1.38 | 0.86 | 0.77 | 1.47 | 4.97 | 0.77 | 1.31 | 3.03 |
| D4 | 0.75 | 1.70 | 1.04 | 0.75 | 1.40 | 0.08 | 0.75 | 1.68 | 1.05 | 0.75 | 1.39 | 0.09 |

The ratios of coloring oxide content (mol %) in enamel: body ("Ratio R Color") are all <1, because the enamel layer has a lighter shade than the body layer. The ratios of coloring oxide+yttria content (mol %) in enamel: body ("Ratio R Color+Y") are all >1, because the enamel layer has a higher yttria content than the body layer, which the coloring oxides do not compensate.

The results in Table 6 show that the Inventive Examples possess a very stable doping ratio enamel: body over all tested colors (D value below 2.70 for all colors).

Such a stable ratio cannot be obtained with the set of powders in the Comparative Examples (D value above 2.70 for rather dark colors).

The Examples all have a "Ratio R Color" between 0.49 and 0.77 for an esthetic color gradient. A number closer to 1 would indicate a slighter gradient, which might be smaller than desired or even difficult to see. A number far below 0.5 might indicate a too pronounced color gradient.

constant ratio defined as varying by a deviation $D_n$ that is not more than 2.70 for all colored mill blanks of the set, $D_n$ is calculated from the ratios $R_n$ of the sum of yttria and coloring ions in mol % between the top layer and the bottom layer with the formula $$D_n=((R_{max}-R_n)/R_{max}*100)/R_{max}^2,$$

with $D_n$ being not more than 2.70 for the differently colored porous zirconia dental mill blanks within the set containing N different colors with $R_{max}$ being the highest ratio found within the set and N≥2, n=1, 2, . . . , N, wherein the dental mill blanks comprise a ratio $R_n$ of (amount of yttria+amount of coloring ions in the top layer in mol %)/(amount of yttria+amount of coloring ions in the bottom layer in mol %) being in a range of 1.83 to 1.67 for a porous zirconia dental mill blank having an yttria gradient from 3.0 to 5.5 mol % from the bottom layer to the top layer, in a range of 1.37 to 1.31 for a porous zirconia dental mill blank having an yttria gradient from 4.0 to 5.5 mol % from the bottom layer to the top layer,
in a range of 1.66 to 1.54 for a porous zirconia dental mill blank having an yttria gradient from 3.0 to 5.0 mol % from the bottom layer to the top layer,
in a range of 1.25 to 1.20 for a porous zirconia dental mill blank having an yttria gradient from 4.0 to 5.0 mol % from the bottom layer to the top layer, or
in a range of 1.76 to 1.62 for a porous zirconia dental mill blank having an yttria gradient from 3.2 to 5.65 mol % from the bottom layer to the top layer.

2. The set of porous zirconia dental mill blanks according to claim 1, the content of yttria in the porous zirconia mill blanks increasing from the bottom layer to the top layer, the content of coloring ions in the porous zirconia mill blanks decreasing from the bottom layer to the top layer.

3. The set of porous zirconia dental mill blanks according to claim 1, the porous zirconia dental mill blanks comprising
$ZrO_2$ from 89.35 to 97.18 mol %,
$HfO_2$ from 0 to 3 mol %,
$Y_2O_3$ from 2.8 to 7.0 mol %,
$Al_2O_3$ from 0 to 0.15 mol %,
coloring ions calculated as their respective oxides from 0.02 to 0.5 mol %,
mol % with respect to the material of the porous zirconia dental mill blank,
the coloring ions being Er and at least one further ion selected from the list of Fe, Tb, V, Mn, Cr, Co.

4. The set of porous zirconia dental mill blanks according to claim 1, the porous zirconia dental mill blanks comprising at least 4 layers.

5. The set of porous zirconia dental mill blanks according to claim 1, the thickness of the individual layers of the porous zirconia dental mill blanks being in a range of 2 to 12 mm.

6. The set of porous zirconia dental mill blanks according to claim 1, the porous zirconia dental mill blanks being characterized by the following features alone or in combination:
Density: 2.8 to 3.2 g/cm³;
Biaxial flexural strength: 8 to 80 MPa;
BET surface: 2 to 20 m²/g;
Vickers hardness: 25 to 150 (HV 0.5) or 35 to 140 (HV 1).

7. The set of porous zirconia dental mill blanks according to claim 1, the porous zirconia dental mill blanks being characterized by the following features:
number of layers: 3 to 7 layers,
yttria concentration difference between the layers being approximately 0.35 mol %,
comprising Er and at least one further coloring ion selected from Fe, Tb, V, Mn, Cr, Co,
yttria concentration: 2.8 to 7.0 mol %, the difference between top layer and bottom layer being at least 1.0 mol %.

8. A process of producing the set of porous zirconia dental mill blanks according to claim 1, the process comprising the steps of
providing at least the following powder compositions:
zirconia powder ZP1 having an yttria content Y1,
zirconia powder ZP2 having an yttria content Y2,
zirconia powder ZP3 containing coloring ions CI-A,
zirconia powder ZP4 containing coloring ions CI-B,
the yttria content Y2 in mol % being higher than the yttria content Y1,
mixing the zirconia powders ZP1, ZP2, ZP3, and ZP4 with different mixing ratios to obtain at least
a zirconia powder composition ZP-MX-B,
a zirconia powder composition ZP-MX-Im,
a zirconia powder composition ZP-MX-T,
the yttria content in mol % of the zirconia powder compositions being
ZP-MX-B<ZP-MX-I$_m$<ZP-MX-T,
the number of intermediate layers being M≥1 with m=1, . . . , M,
for each colored porous zirconia dental mill blank of the set layering the zirconia powder compositions in the cavity of a mould so that
the layer of ZP-MX-B is located below the layer(s) of ZP-MX-I$_m$,
the layer(s) of ZP-MX-I$_m$ is located below the layer of ZP-MX-T
compacting the layered zirconia powder compositions,
optionally heat-treating the compacted zirconia powder compositions.

9. The process according to claim 8, the layer thickness of the zirconia powder composition layers being as follows:
ZP-MX-B>ZP-MX-I$_m$<ZP-MX-T.

10. A process of producing a dental restoration, the process comprising the steps of
providing the set of porous zirconia dental mill blanks according to claim 1,
selecting from the set a porous zirconia dental mill blank,
machining a porous dental restoration precursor from the porous zirconia dental mill blank,
sintering the porous dental restoration precursor to obtain a dental restoration.

11. The process according to claim 10, the dental restoration being characterized by the following features alone or in combination:
density: 5.8 to 6.1 g/cm³;
translucency: at least 30%, measured in reflection mode, averaged over a wavelength of 400 to 700 nm determined on a sample having a thickness of 1 mm and being cut from the top layer of the dental zirconia mill blank;
translucency: at least 15%, measured in reflection mode, averaged over a wavelength of 400 to 700 nm determined on a sample having a thickness of 1 mm and being cut from the bottom layer of the dental zirconia mill blank.

12. A kit of parts comprising the set of porous zirconia dental mill blanks according to claim 1, and a dental cement.

13. The set of porous zirconia dental mill blanks according to claim 1, the yttria content of the differently colored porous zirconia dental mill blanks differing from layer to layer by an amount in the range of 0.35 to 0.45 mol %.

14. The set of porous zirconia dental mill blanks according to claim 1,
wherein the yttria content increases from the bottom layer to the top layer by increments not exceeding 0.5 mol % per layer, and wherein the coloring ions content decreases from the bottom layer to the top layer, resulting in a total coloring ions content ranging from approximately 0.02 to 0.5 mol %.

* * * * *